United States Patent [19]
Flower

[11] Patent Number: 6,047,208
[45] Date of Patent: Apr. 4, 2000

[54] IONTOPHORETIC CONTROLLER

[75] Inventor: Ronald J. Flower, Lawrenceville, Ga.

[73] Assignee: Becton, Dickinson and Company, Franklin Lakes, N.J.

[21] Appl. No.: 08/924,764

[22] Filed: Aug. 27, 1997

[51] Int. Cl.$^7$ .................................................. A61N 1/30
[52] U.S. Cl. ................................................. 604/20; 604/65
[58] Field of Search ............................ 604/20, 65, 67; 607/152, 1–3, 59, 62

[56] References Cited

U.S. PATENT DOCUMENTS

| | | | |
|---|---|---|---|
| 4,822,334 | 4/1989 | Tapper ........................................ | 604/20 |
| 5,047,007 | 9/1991 | McNichols et al. ....................... | 604/20 |
| 5,213,568 | 5/1993 | Lattin et al. ............................... | 604/20 |
| 5,224,928 | 7/1993 | Silbalis et al. ............................. | 604/20 |
| 5,246,418 | 9/1993 | Haynes et al. ............................. | 604/20 |
| 5,306,235 | 4/1994 | Haynes ....................................... | 604/20 |
| 5,571,149 | 11/1996 | Liss et al. .................................. | 607/72 |

*Primary Examiner*—Corrine McDermott
*Attorney, Agent, or Firm*—Arthur D. Dawson

[57] ABSTRACT

An iontophoretic controller is provided. The controller is electrically connected via two electrical connectors to a patch consisting of two electrodes, the two electrodes are respectively positioned in an active reservoir and a return reservoir of the patch. A current is applied to the patch when the iontophoretic controller is turned on or otherwise activated. A waveform, such as the patch voltage, is measured over a predetermined time interval. A change in the measured voltage is compared to a threshold. If the change in measured voltage exceeds the threshold, the controller takes an action, such as providing a warning or discontinuing the application of current.

18 Claims, 9 Drawing Sheets

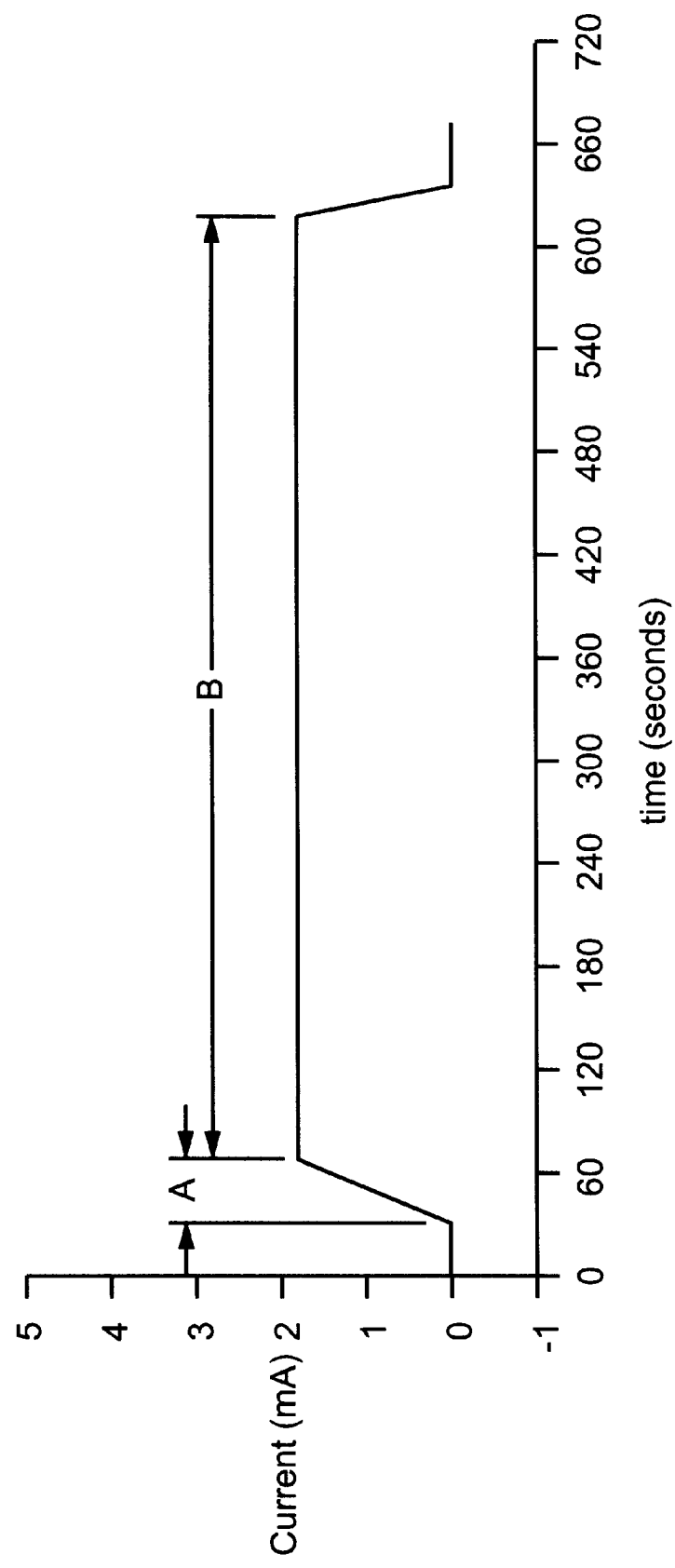

IONTOPHORETIC CONTROLLER

BACKGROUND OF THE INVENTION

1. Field of the Invention

The invention is in the field of iontophoresis. In particular, the invention relates to an iontophoretic drug delivery system, having an iontophoretic controller and patch, which automatically detects when certain events or conditions occur in the system. Such events or conditions may include the substantial depletion of the conductive material of the electrodes of the iontophoretic patch or failure of the iontophoretic controller. In response to the detection of an event or condition, such as, for example, a fault, the system performs an action such as providing a warning or stopping the supply of iontophoretic current to the iontophoretic patch.

2. Description of Related Art

Iontophoresis is the application of an electrical current to transport ions through intact skin; the ionized species are usually the ionic form of a drug or other therapeutic agent. One particularly advantageous application of iontophoresis is the non-invasive transdermal delivery of ionized drugs into a patient. This is done by applying current to the electrodes of the iontophoretic patch. The electrodes are respectively arranged within a drug reservoir, containing the drug ions, and a return reservoir, containing an electrolyte. When the patch is placed on skin of a patient, current applied from the iontophoretic current controller forces the ionized drug contained in the drug reservoir through the skin and into the patient. Iontophoretic drug delivery offers an alternative and effective method of drug delivery to other drug delivery methods such as passive transdermal patches, needle injection, and oral ingestion, and is an especially effective method for children, the bedridden and the elderly.

Typically, during iontophoresis, as a constant, controlled current is applied through the patch (current-time curve, FIG. 1A, portion B), the voltage across the patch monotonically decreases as a function of time (voltage-time curve, FIG. 1B, portion B) due to decreasing skin impedance during the process (resistance-time curve, FIG. 1C, portion B). (The initial increase in voltage, portion A of FIG. 1B, is a transient state caused by turning on the patch, as will be explained in more detail below.) There may also be occasional small amplitude, short duration, increases or decreases in the voltage due to patient or patch movement or due to electrical noise (not shown).

However, certain conditions can cause a relatively larger amplitude, longer duration, change (up-ramping or down-ramping) of the voltage. These conditions include, but are not necessarily limited to: poor contact between the patch and skin, the patch being substantially depleted of drug or other ions, the patch being substantially depleted of electrode material, certain failures of the iontophoretic current controller, an improper electro-chemical reaction, damage to the patch or contacts, and excessive electrical noise from some external source. Moreover, a patient may attempt to reuse a patch having a substantially depleted electrode or drug reservoir, which would also cause an undesirable large amplitude, long duration, voltage increase.

All of these conditions may interfere with the safe and effective iontophoretic delivery of the drug to the patient. Moreover, when the voltage suddenly changes, the patient may feel an uncomfortable sensation at or near where the patch is attached.

SUMMARY OF THE INVENTION

The present invention advantageously provides an iontophoretic drug delivery system that overcomes the above-described problems by automatically performing an action, such as, for example, performing a warning or stopping the supply of current, when a sufficient up-ramping of voltage has been detected by the controller, thus preventing patient discomfort or drug misdelivery.

In one aspect of the present invention, an iontophoretic system having an iontophoretic controller and patch are provided. The controller is electrically connected to the two patch electrodes via two electrical connectors, the two electrodes respectively being positioned in an active (drug) reservoir and the return reservoir of the patch. The controller includes a current source for supplying current to the electrodes when the controller is turned on, a voltage measuring device for measuring a change in voltage over a predetermined time interval and a comparator for comparing the measured change in voltage to a threshold. The supply of current is stopped, or a warning or some other action is taken, when the comparator determines that the change in voltage over the predetermined time interval exceeds the threshold.

In another aspect of the present invention, the iontophoretic controller includes a device for measuring the supplied current over a predetermined time interval, and a comparator compares a measured change in current to a current threshold. In this aspect of the invention, the controller takes action when the comparator determines that the measured change in current over the predetermined time interval exceeds the current threshold.

In yet another aspect of the present invention, the iontophoretic controller includes a device for determining a load impedance from a measured patch voltage and current. The change in load impedance over a predetermined time interval is determined, and a comparator compares the measured current to an impedance threshold. In this aspect of the invention, the controller takes action when the comparator determines that the measured change in impedance over the predetermined time interval exceeds the impedance threshold.

BRIEF DESCRIPTION OF THE DRAWINGS

These and other features and advantages of the present invention can best be understood by reference to the detailed description of the preferred embodiments set forth below taken with the drawings, in which:

FIGS. 1A, 1B and 1C are curves respectively illustrating the patch electrode current over time, the corresponding patch electrode voltage measured over time, and the resistance of the iontophoretic patch calculated from the electrode current and voltage.

DETAILED DESCRIPTION OF THE PREFERRED EMBODIMENTS

Figure 2:
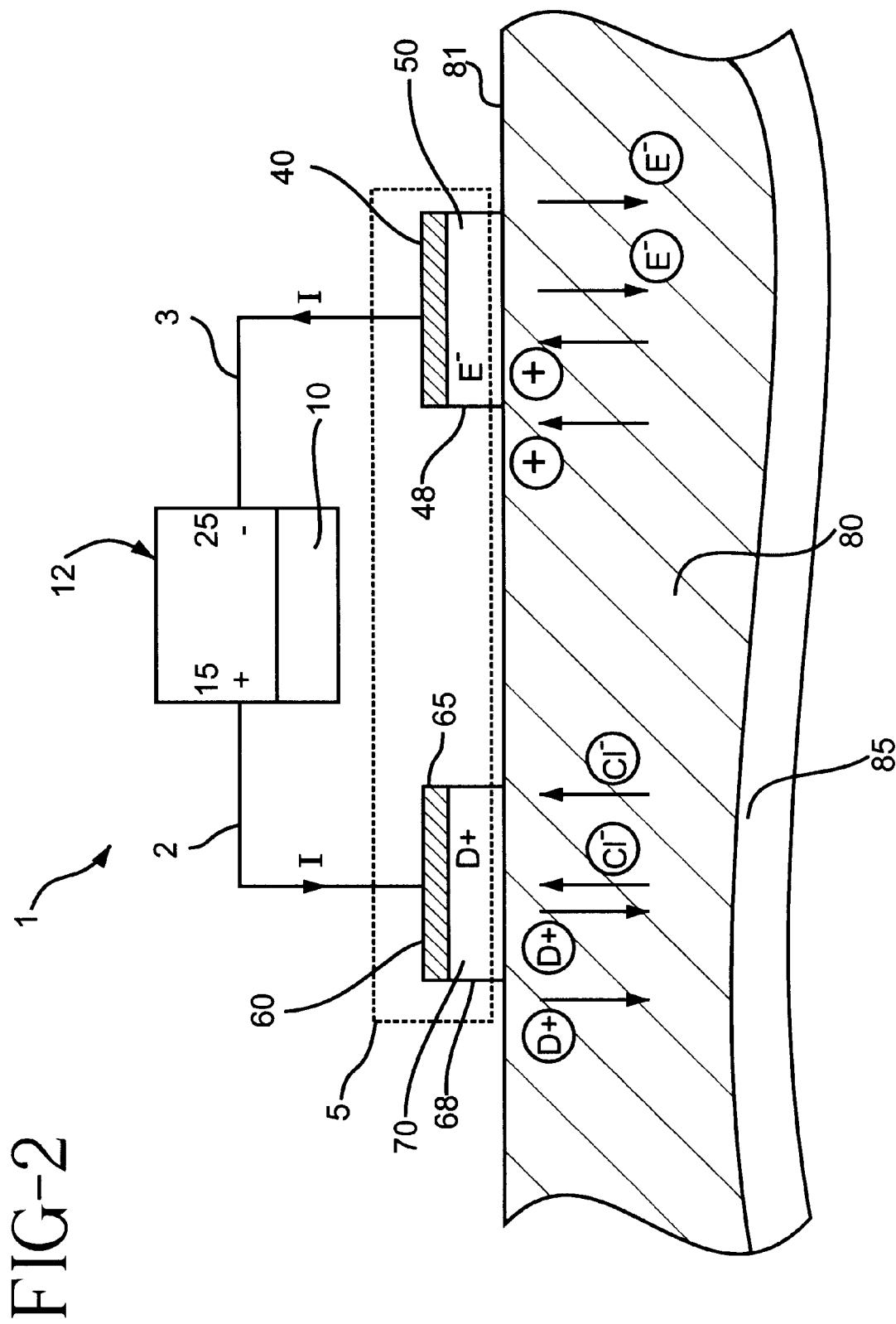
FIG. 2 illustrates an iontophoretic system according to the present invention.

The embodiments of the present invention relate to an iontophoretic delivery system 1 illustrated in FIG. 2. The iontophoretic delivery system shown in FIG. 2 includes a current controller 12 containing an energy source, such as a battery 10, and connected to a patch 5. The patch 5 has an active reservoir 68 and a return reservoir 48 respectively containing a drug $D^+$ and an electrolyte. The patch 5 also includes a first electrode 60 (an anode), arranged inside the active reservoir 68, and a second electrode 40 (a cathode) arranged inside the return reservoir 48, respectively in contact with the drug and the electrolyte. Alternatively, if the ionic charge of the drug is negative, that is, $D^-$, then electrode 60 will be the cathode and electrode 40 will be the anode.

Electrical connectors 2 and 3 respectively carry current between the electrodes 60 and 40 and the controller 12. When patch 5 is placed on skin 81 of the patient 80, and the controller 12 is turned on to supply current to the electrodes 60 and 40 of patch 5, the drug $D^+$ passes through the skin 81 into the patient 80 because the patient's body completes the iontophoretic circuit.

It is desirable for the controller to take some action when the electrode becomes depleted of conductive material during a treatment, or when a patch already having a spent electrode is mistakenly reused. It is also desirable for the controller to act when there is an indication that the controller is not operating properly. It is also desirable to act if the patch becomes partially or completely disconnected from the skin or is damaged.

As described above, these and other faulty conditions generally result in the same effect—an up-ramping of voltage. In the present invention, the controller is provided with circuitry for detecting this up-ramping voltage. Upon detection, the controller then automatically takes an action, such as setting off an audio, visual or tactile alarm, or providing some other warning or indication. Alternatively, the supply of current to the patch may be discontinued.

Figure 1B:
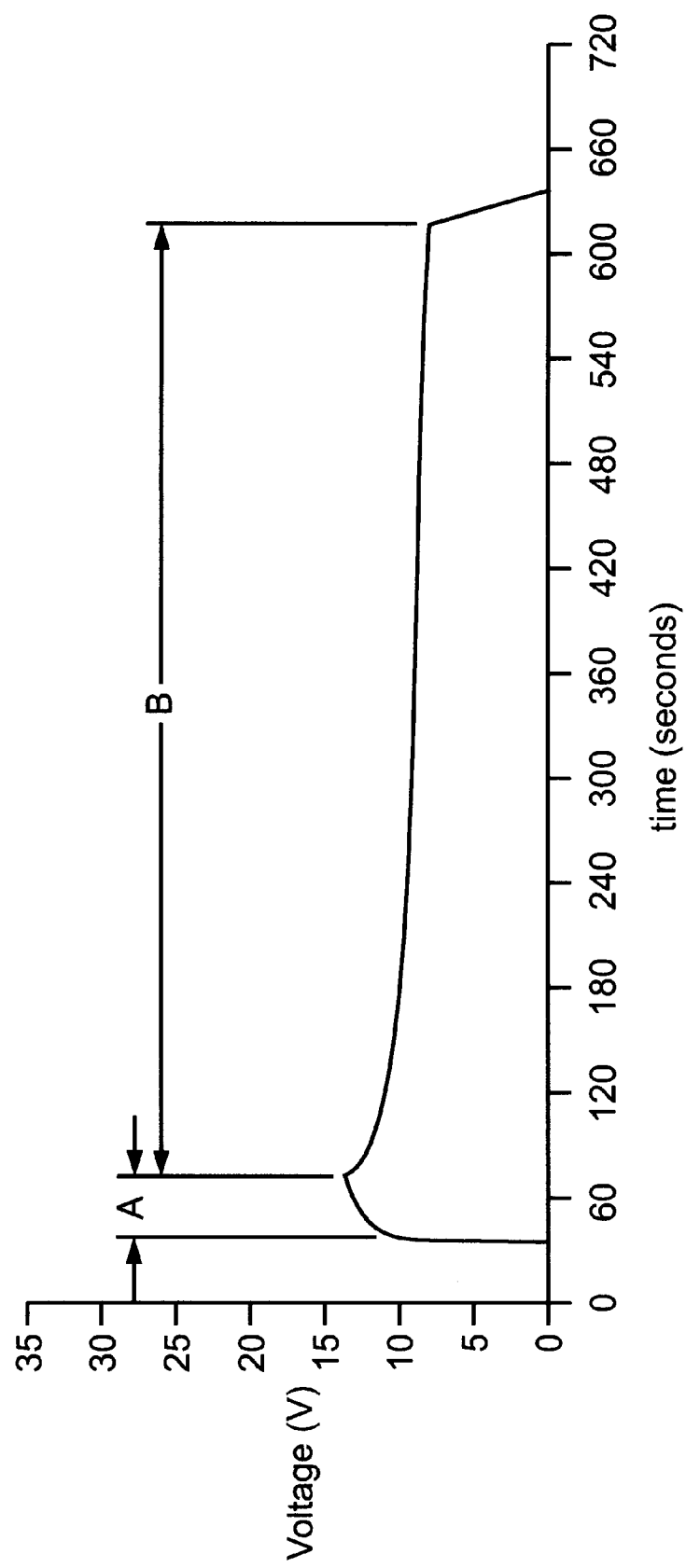
Figure 1C:
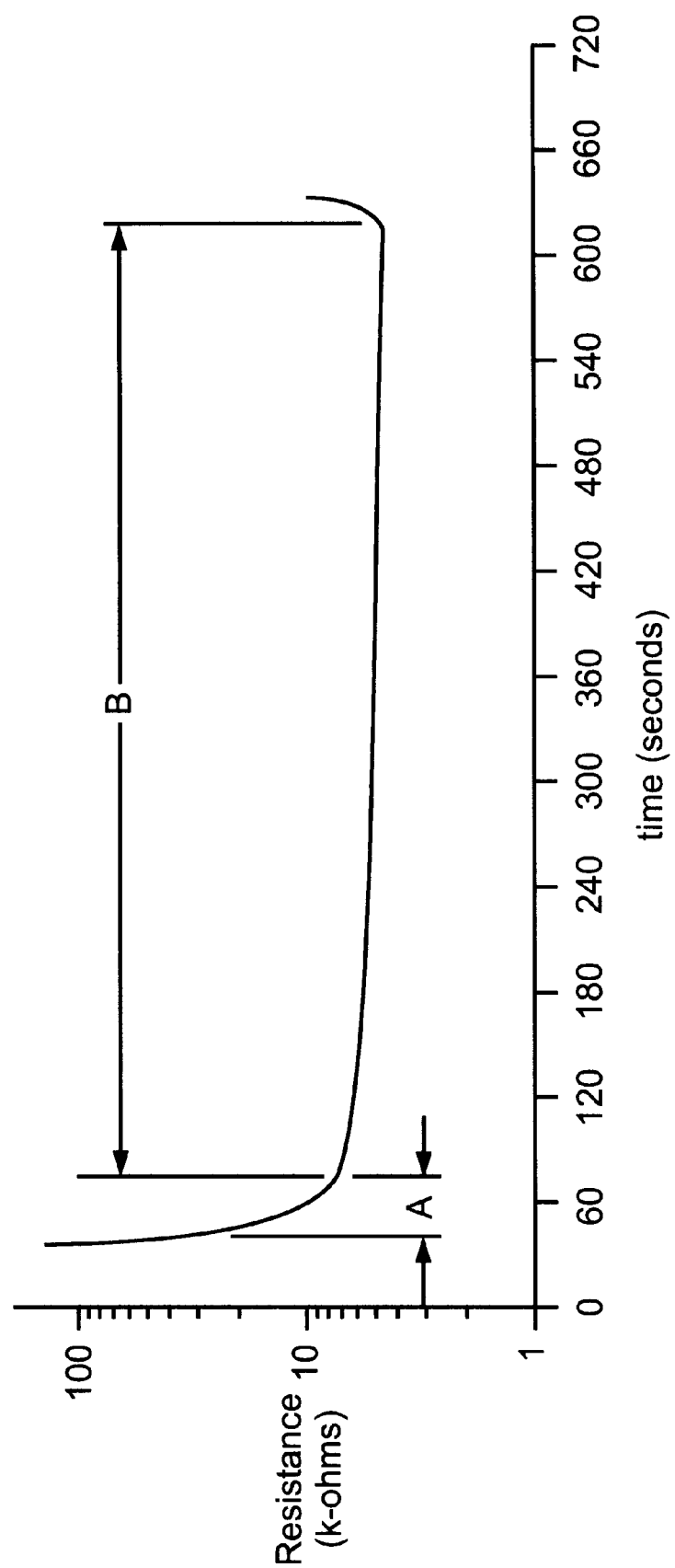

FIG. 1A, as explained above, shows an example of the delivered patch current over time during iontophoresis, and FIG. 1B shows the corresponding measured voltage. FIG. 1C shows the resistance of the patch over time, calculated from the measured patch current and voltage. In further detail, in the initial portion A of FIGS. 1A, 1B and 1C, as the current increases, the voltage increases and the resistance decreases. In portion B of FIGS. 1A, 1B and 1C, as the current remains constant, the voltage and resistance both monotonically decrease with time. This example assumes that a constant rate of current is required to deliver a constant rate of drug (in iontophoresis, it is known that the amount of drug delivered is proportional to the amount of supplied current) during most of the delivery cycle. One skilled in the art will appreciate, however, that non-constant drug delivery profiles, and thus non-constant current profiles are also possible. Even when constant current is being supplied to the patch in a steady state, the voltage continues to decrease as the skin impedance decreases. At this point in time, the impedance of the electrode is relatively small and can be neglected.

When the patch becomes substantially depleted of electrode material, the electrode impedance substantially increases because of the large reduction in conductive surface area. This increasing impedance causes an up-ramping in the measured patch voltage, since the current is controlled to remain substantially constant.

To detect this rapidly increasing change in voltage, that is, the positive slope of the voltage curve, the controller 12 includes circuitry to measure the voltage across the electrodes at predetermined intervals and compare the change in the measured voltage to a predetermined threshold. If the change exceeds the predetermined threshold, the controller then takes an action, or stops supplying current to the patch. Because there can be a large positive voltage slope during the initial transient period, the measured change in voltage is not compared to the threshold until steady-state drug delivery has already begun.

Figure 3A:
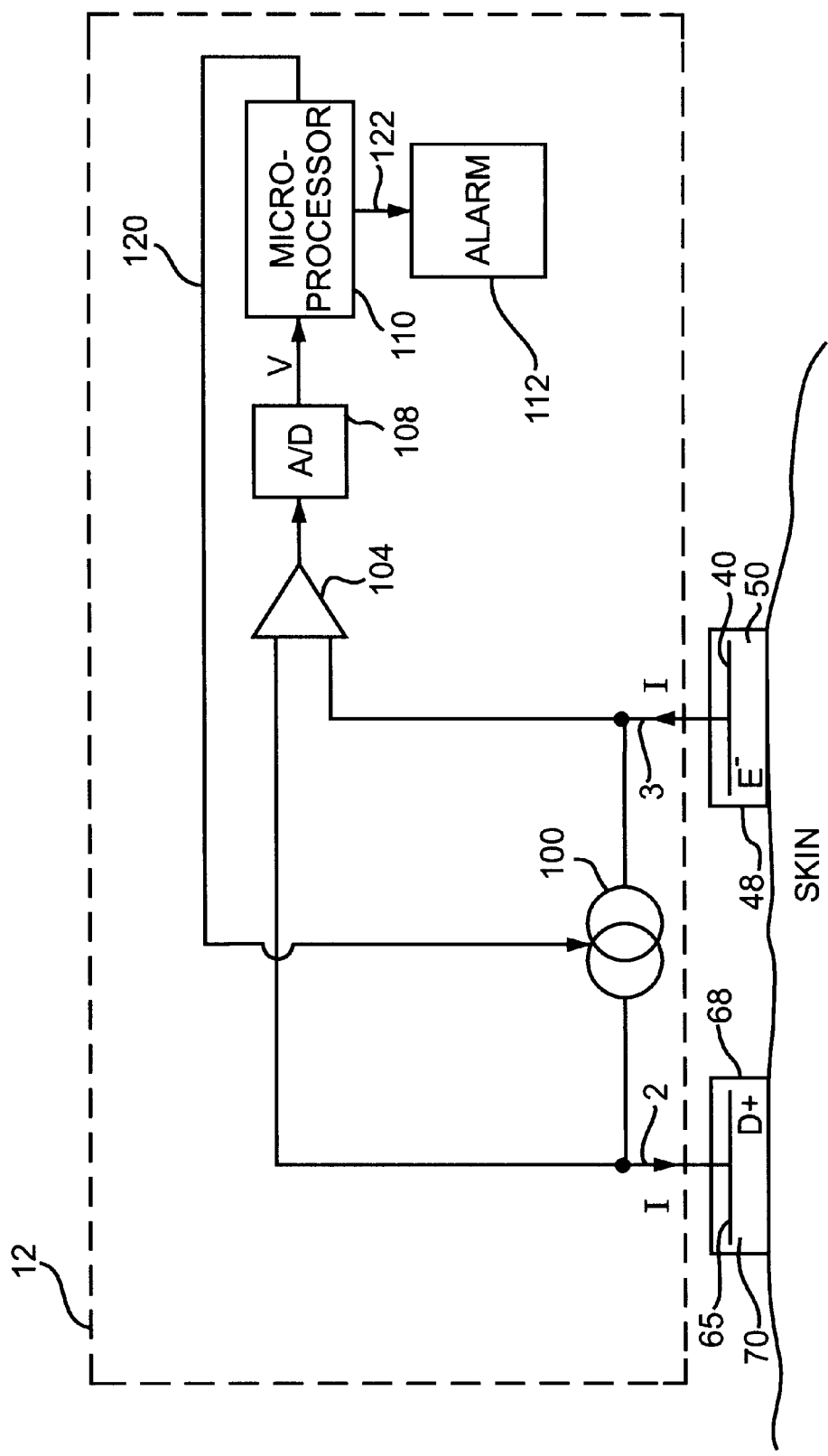
FIG. 3A illustrates circuitry for measuring patch voltage and for detecting an up-ramping of the voltage in accordance with a first embodiment of the present invention.

The controller circuitry for controlling the current, measuring the patch voltage V and comparing the measured voltage to a threshold is shown in FIG. 3A. Current I is supplied to the patch by current source 100. Differential amplifier 104 measures the voltage V across the patch. The analog voltage measurements are converted to digital values by the analog to digital (A/D) converter 108 and read by a microprocessor 110. The microprocessor controls the time interval between voltage measurements, calculates a difference between the voltage measurements and compares this voltage difference to a predetermined (voltage) threshold, as will be explained in more detail below in reference to FIGS. 4 and 5. When the voltage difference exceeds the predetermined threshold, an error condition is said to exist, and the microprocessor turns off the current source 100 through control line 120, or activates an alarm 112 through control line 122, or both.

It is to be appreciated that this is not the only way to accomplish this task. For example, a comparison of the voltage to the predetermined threshold may be performed in hardware by a voltage comparator and a state machine, as well as by software in the microprocessor.

In addition, means may be provided for switching between the connected patch and an auxiliary, unconnected patch. These means may include a microprocessor-controlled, logic-controlled or mechanical switch connected to those two patches. In this case, the action taken by the controller upon the measured or computed parameter exceeding a threshold would be to cause the switch to disconnect the presumably faulty patch and connect the auxiliary patch to the controller.

Figure 3B:
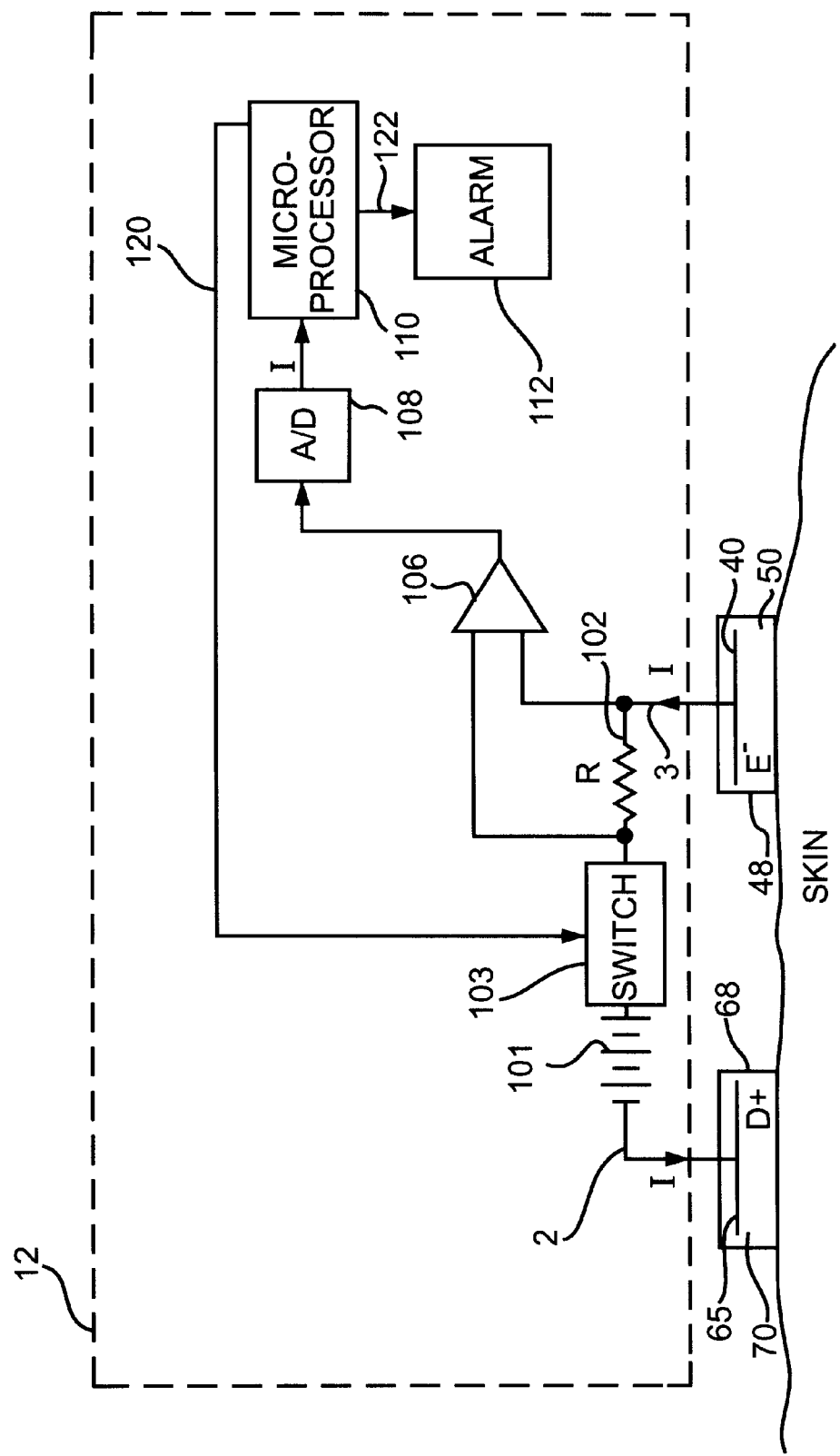
FIG. 3B illustrates circuitry for measuring supply current and for detecting an up-ramping of the current in accordance with a second embodiment of the present invention.

In a second embodiment of the present invention, shown in FIG. 3B, the patch voltage is controlled, while the supply current I is measured and comparing the measured voltage to a threshold is shown in FIG. 3A. Current I is supplied to the patch by battery 101 through a current sensing resistor 102 when switch 103 is closed. Switch 103 may be any type of switch, but is preferably configured as a MOSFET. Differential amplifier 106 measures the voltage across the current sensing resistor 102, $V_R$, thereby measuring the current I flowing through the patch, equal to $V_R/R$. The analog current measurements are converted to digital values by the A/D converter 108 and read by the microprocessor 110. In a fashion similar to the first embodiment described above, the microprocessor controls the time interval between current measurements, takes a difference between the current measurements and compares this current difference to a predetermined (current) threshold. When the current difference exceeds the predetermined threshold, an error condition is said to exist, and the microprocessor through control line 120 turns off the current I by opening switch 103, or activates an alarm 112 through control line 122, or both.

Figure 3C:
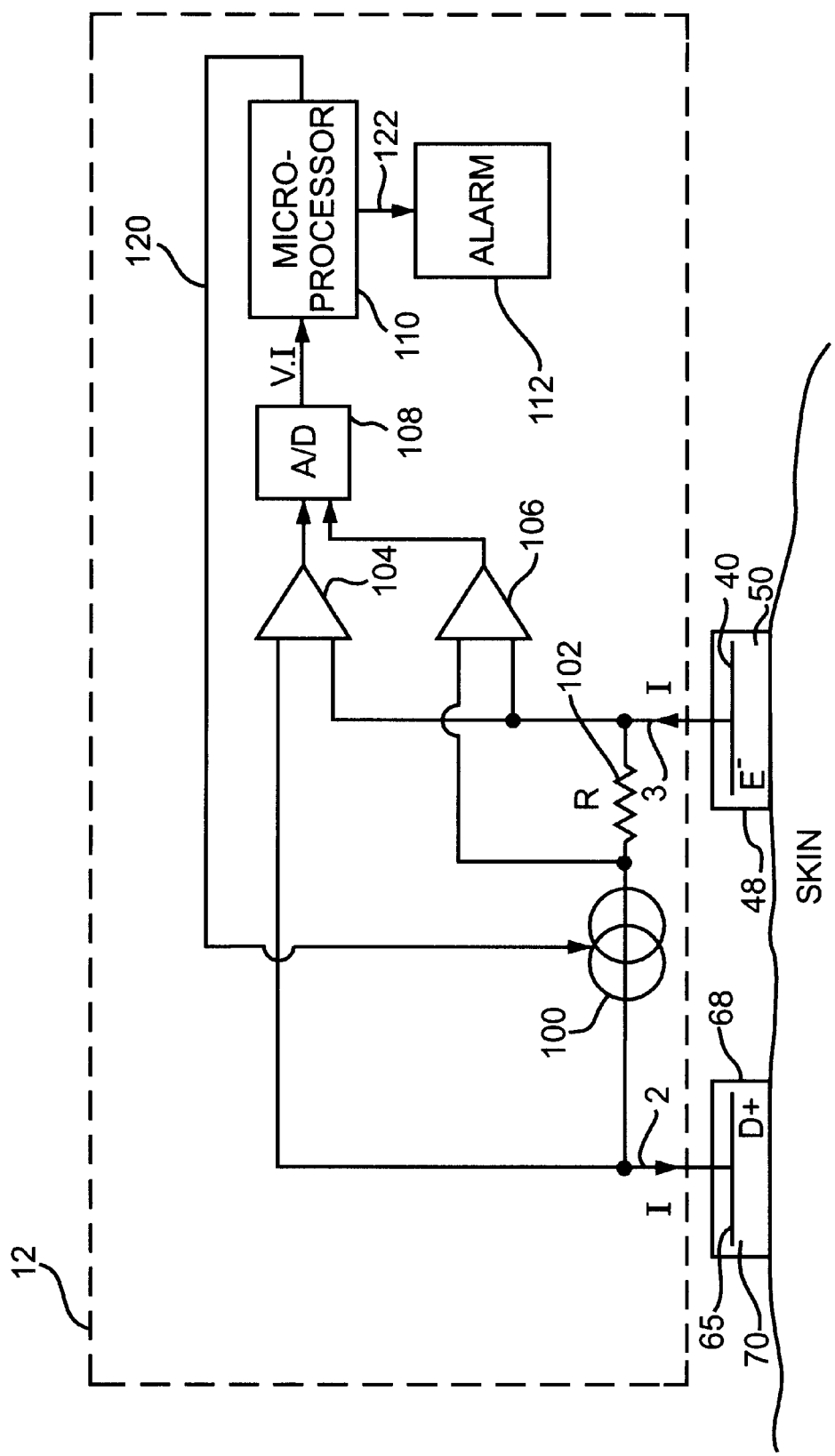
FIG. 3C illustrates circuitry for measuring load impedance, and for detecting an up-ramping of the load impedance in accordance with a third embodiment of the present invention.

Alternatively, in a third embodiment shown in FIG. 3C, the current is controlled, both patch voltage V and current I are measured, and a load impedance (V/I) is calculated therefrom. Current I is supplied to the patch by current source 100. Differential amplifier 104 measures the voltage V across the patch and differential amplifier 106 measures the voltage across the current sensing resistor 102, $V_R$, thereby measuring the current I flowing through the patch, equal to $V_R/R$. The analog voltage measurements are converted to digital values by the analog to digital (A/D) converter 108 and read by a microprocessor 110. In this embodiment, the A/D converter output is multiplexed to provide selectively digital voltage V and current I values. The microprocessor controls the time interval between voltage or current measurements. The microprocessor computes a load impedance from a digital voltage measurement and a digital current measurement determined at a given time. The microprocessor then calculates a difference between two load impedances computed respectively at two different times and compares this load impedance difference to a predetermined (load impedance) threshold. When the load impedance difference exceeds the predetermined threshold, an error condition is said to exist, and the microprocessor turns off the current source 100 through control line 120, or activates an alarm 112 through control line 122, or both.

Figure 4:
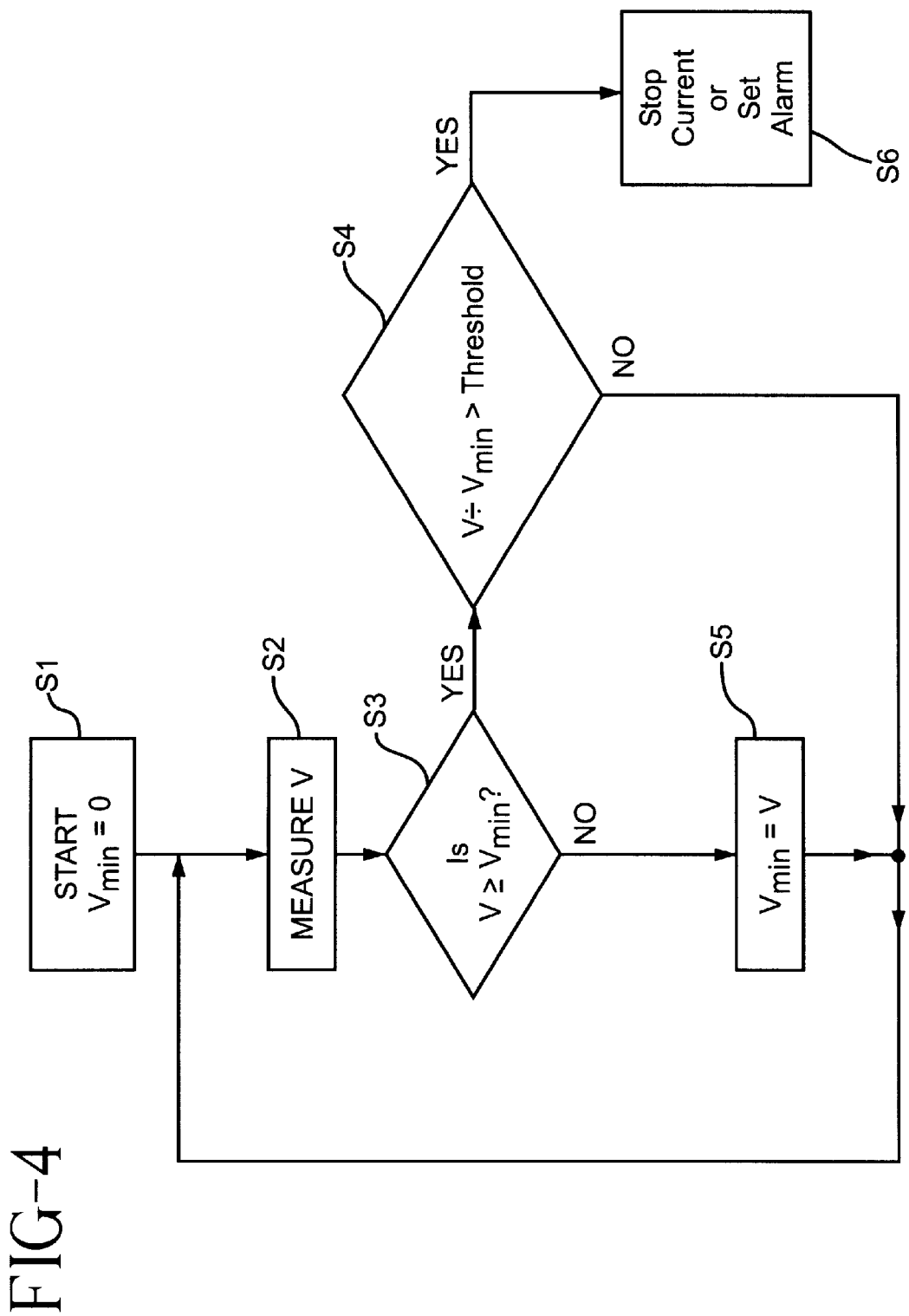
FIG. 4 illustrates a flowchart of a method for detecting an up-ramping of voltage in accordance with a fourth embodiment of the present invention.

In a fourth embodiment of the invention, a method for monitoring the patch voltage as measured by the circuit of FIG. 3A is illustrated by the flowchart of FIG. 4. This method is based on the above-described premise that in steady-state, constant current delivery, the measured voltage is expected to monotonically decrease, and that a problem may have occurred if the measured voltage rises above a minimum measured voltage by a predetermined amount. In step S1, one end of the patch is attached to the patient while the other end of the patch is inserted into the controller. The controller is switched on, either manually or automatically, supplying current to the patch. In step S2, after steady-state iontophoresis has been achieved after a predetermined amount of time, the above-described controller circuitry measures the voltage across the electrodes of the patch over a predetermined time interval, for example, one second. In step S3 the controller compares this voltage to the lowest voltage, $V_{min}$, thus far measured. If the measured voltage is greater than or equal to $V_{min}$, then in step S4 the controller compares the difference between the measured voltage and the minimum measured voltage to the predetermined threshold value (V-$V_{min}$>threshold). If not, the measured voltage has decreased as compared to the lowest voltage thus measured, and thus $V_{min}$ is set to that measured voltage in step S5, and the controller continues to measure the voltage in step S2. As stated above, in step S4, the controller compares the difference between the measured voltage and the minimum measured voltage to the predetermined threshold, for example, +N volts. If that difference has not exceeded the predetermined threshold, then step S2 is repeated. On the other hand, if the difference exceeds the predetermined threshold, some problem may have occurred, and the current supplied to the patch is stopped or some other action is taken, as indicated by step S6.

Figure 5:
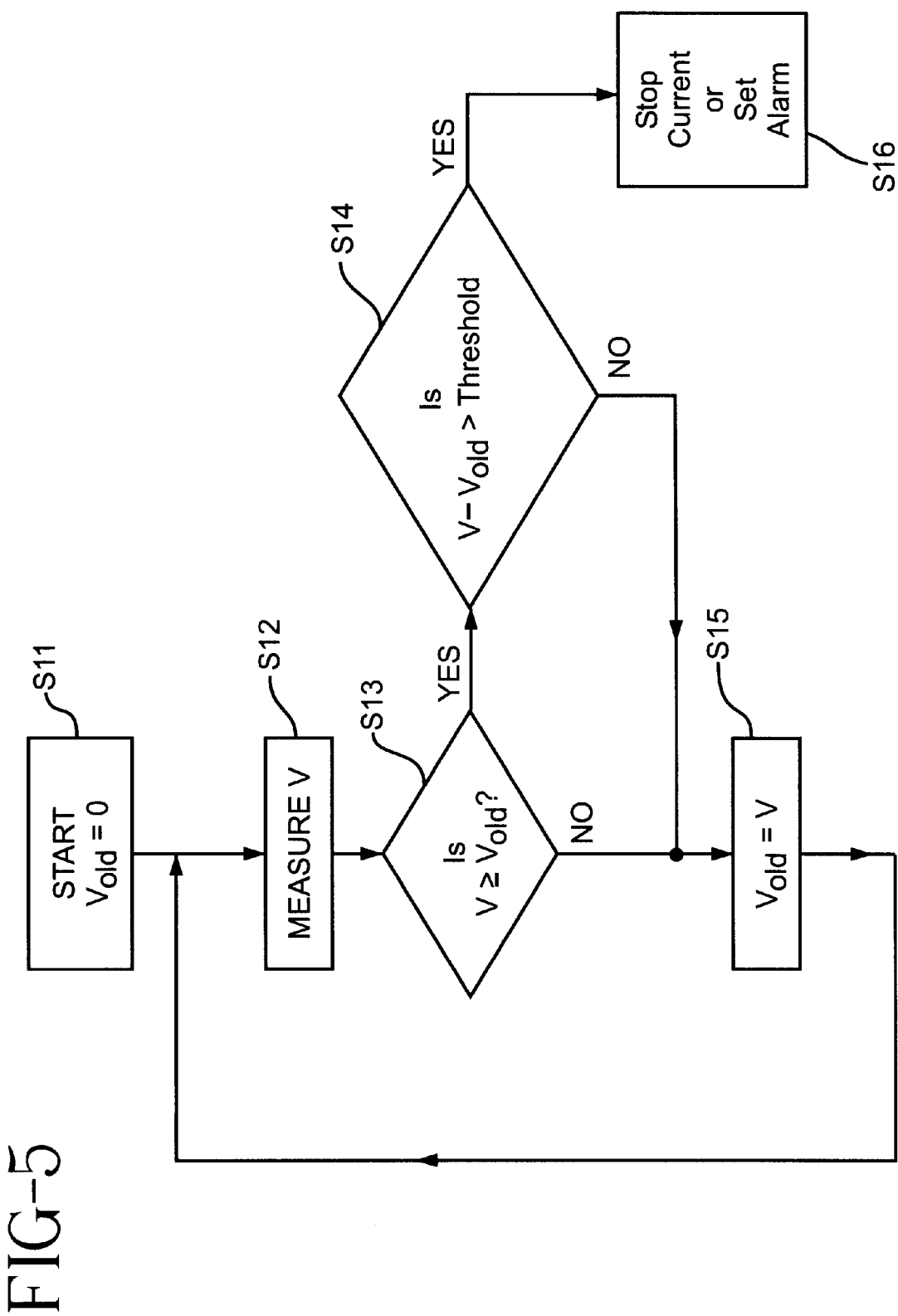
FIG. 5 illustrates a flowchart of another method for detecting an up-ramping of voltage in accordance with a fifth embodiment of the present invention.

In a fifth embodiment of the invention, another method for monitoring the patch voltage as measured by the circuit of FIG. 3A is illustrated by the flowchart of FIG. 5. This method is based on the above-described premise that in steady-state, constant current delivery, the voltage slope is expected to decrease, and that a problem may have occurred if the measured voltage slope increases by a predetermined amount. In step S11, one end of the patch is attached to the patient while the other end of the patch is inserted into the controller. The controller is switched on, either manually or automatically, supplying current to the patch. In step S12, after steady-state iontophoresis has been achieved after a predetermined amount of time, the above-described controller circuitry measures the voltage across the electrodes of the patch over a predetermined time interval, for example, one second. In step S13 the controller compares the current voltage sample (V) to the previous voltage sample, $V_{old}$. If V is greater than or equal to $V_{old}$, then in step S14 the controller compares the change in voltage between samples to a predetermined slope threshold value (V-$V_{old}$>slope threshold). If not, $V_{old}$ is set to the current voltage sample V in step S15, and the controller continues to measure the voltage in step S12. As stated above, in step S14, the controller compares the difference between the current and previous voltage samples to the predetermined slope threshold, for example, +N volts per unit of time, such as, for example, one second intervals. In essence, the comparison is between the measured instantaneous voltage slope and the voltage slope threshold. If the difference has not exceeded the predetermined slope threshold, then $V_{old}$ is set to the current voltage sample V in step S15, and the controller continues to measure the voltage in step S12. On the other hand, if the difference exceeds the predetermined voltage slope threshold, then some problem may have occurred, and the current supplied to the patch is stopped or some other action is taken, as indicated by step S16. Alternatively, the slope threshold may be a large negative number, indicating that a large drop in voltage has occurred. This too may indicate that a problem has occurred, or simply that the delivery cycle is over if current is no longer being supplied through the patch. In either case, a warning or some other action may be taken at that time.

Variations in the method illustrated by FIG. 5 may include the following. For example, the controller may determine only whether a change in the "sign" (from negative to positive) of the difference between V and $V_{old}$ has occurred. This is equivalent to setting the predetermined slope threshold to zero volts/sec. This variation is sensitive to any positive changes in voltage. However, in this case, a small positive voltage change caused by patient movement or electrical noise may cause the controller to take action or to turn off the current before the electrode is actually depleted. In addition, the controller may require that the difference V-$V_{old}$ exceeds the predetermined slope threshold and that V itself exceed a minimum voltage threshold before it takes action.

Alternatively, as described above in FIG. 3B, the supplied current may be measured by the controller. In this case, the above-described methods of FIGS. 4 and 5 would use the measured currents instead of the measured voltages. Alternatively, as described in connection with FIG. 3C, both the patch voltage and the supplied current may be measured and a load impedance calculated therefrom. In this case, the above-described methods of FIGS. 4 and 5 would use the calculated load impedances instead of the measured voltages. In general, it will be appreciated that any of the various combinations of voltage V, voltage difference (V-$V_{min}$ or V-$V_{old}$), current I, current difference (I-$I_{min}$ or I-$I_{old}$), impedance Z, and impedance difference (Z-$Z_{min}$ or Z-$Z_{old}$) may be used to detect whether a problem may have occurred.

Of course, it will be appreciated that the invention may take forms other than those specifically described above.

For example, any combination of voltage, current or impedance may be measured, compared and acted upon. Further, the source of power may be a constant or time-varying power source, and may be a current source, a voltage source or a Thevenin equivalent source. In addition, the voltage slope threshold or the voltage threshold, or both, or any other threshold, may be predetermined, or may be automatically determined by the controller. Methods for automatically determining thresholds are known to those skilled in the signal processing art.

Moreover, the device may measure the voltage, current or impedance waveform over a predetermined time interval, and a matched filter or correlator circuit may be used to detect any significant variance of the measured voltage, current or impedance waveform from a respective expected voltage, current or impedance waveform.

While the preferred embodiments of the present invention have been described so as to enable one skilled in the art to practice the devices and methods of the present invention, it is to be understood that variations and modifications may be employed without departing from the concept and intent of the present invention as defined in the following claims. The preceding description is intended to be exemplary and should not be used to limit the scope of the invention. The scope of the invention should be determined only by reference to the following claims.

What is claimed is:

1. An iontophoretic controller, connectable to a patch having a plurality of electrodes via a respective plurality of electrical connectors, at least two of said plurality of electrodes respectively positioned in an active reservoir and a return reservoir of the patch, said controller comprising:

a power source having a plurality of connectors attachable to a plurality of electrodes on the patch when the patch is disposed on a patient for supplying power to the patch so that the patch provides a measurable waveform to the controller through said connectors in response to an impedance of the patient;

means for measuring a voltage waveform and a current waveform of the patch, and Generating an impedance waveform therefrom over a predetermined time interval; and means for comparing said impedance waveform to a predetermined impedance waveform, wherein said controller takes an action when said comparing means detects a difference between the generated waveform and the predetermined waveform.

2. An iontophoretic controller according to claim 1, wherein said power source comprises one of a group of a current source, a voltage source and a Thevenin equivalent source.

3. An iontophoretic controller, connectable to a patch having a plurality of electrodes via a respective plurality of electrical connectors, at least two of said plurality of electrodes respectively positioned in an active reservoir and a return reservoir of the patch, said controller comprising:

means, having a plurality of connectors, for supplying a current through the patch through the plurality of connectors to the plurality of electrodes when said controller is activated and said controller is connected to the patch;

means for measuring a change in a voltage, related to said supplied current, across the patch over a predetermined time interval; and means for comparing the measured change in voltage to a threshold, wherein said controller takes an action when said comparing means determines that the change in measured voltage exceeds the threshold determined from prior voltage measurements.

4. An iontophoretic controller according to claim 3 wherein the threshold is a predetermined positive number.

5. An iontophoretic controller according to claim 3, wherein the action taken is a warning action.

6. An iontophoretic controller according to claim 5, wherein the warning action comprises causing an audio alarm.

7. An iontophoretic controller according to claim 5, wherein the warning action comprises causing a visual alarm.

8. An iontophoretic controller according to claim 5, wherein the warning action comprises causing a tactile alarm.

9. An iontophoretic controller according to claim 3 wherein the action taken includes discontinuing the supply of the current by said current supplying means.

10. An iontophoretic controller according to claim 3, further comprising means for switching between the patch and an auxiliary patch, and the action taken is a switching between the patch and the auxiliary patch.

11. An iontophoretic controller according to claim 3, wherein the comparison is performed by said comparing means after the supply of current has reached a steady state.

12. An iontophoretic controller according to claim 3, wherein the change in voltage is determined from a presently measured voltage and a previously measured voltage.

13. An iontophoretic controller according to claim 12, wherein the previously measured voltage is a minimum previously measured voltage.

14. An iontophoretic controller according to claim 3, wherein said current supplying means comprises a current source, said voltage measuring means comprises a differential amplifier to measure the voltage across the patch and an analog to digital converter to convert the measured to a digital voltage, and said comparing means comprises a microprocessor to compare the digital voltage values.

15. An iontophoretic controller connectable to a patch having a plurality of electrodes via a respective plurality of electrical connectors, at least two of said plurality of electrodes respectively positioned in an active reservoir and a return reservoir of the patch, said controller comprising:

means, including a power source having a plurality of connectors, comprising a battery serially connected to a switch connected by the plurality of connectors to the plurality of electrodes, for controlling a voltage across the patch when said controller is activated and said controller is connected to the patch;

means for measuring a chance in a current, comprising a resistor, a differential amplifier for measuring the voltage across said resistor so as to measure the current, and an analog to digital converter for converting the measured current to a digital current value, related to said voltage across said patch, supplied through the patch over a predetermined time interval; and means for comparing the measured change in current to a threshold, comprising a microprocessor which compares the digital current values, wherein said controller takes an action when said comparing means determines that the change in measured current exceeds the threshold.

16. An iontophoretic controller according to claim 15, wherein the action taken includes stopping the application of voltage by opening said switch.

17. An iontophoretic controller, connectable to a patch having a plurality of electrodes via a respective plurality of electrical connectors, at least two of said plurality of electrodes respectively positioned in an active reservoir and a return reservoir of the patch, said controller comprising:

means for supplying a current comprising a current source and a plurality of connectors, through the plurality of connectors to the plurality of electrodes through the patch when said controller is activated and said controller is connected to the patch;

means for measuring a change in a voltage related to said supplied current, comprising a differential amplifier to measure the voltage across the patch over a predetermined time interval and an analog to digital converter to convert the measured voltage to a digital voltage value;

means for measuring a change in said current supplied through the patch comprising a resistor, a different amplifier for measuring the voltage across said resistor so as to measure the current over said predetermined time interval, and the analog to digital converter for converting the measured current to a digital current value;

means for computing a change in load impedance from the measured change in voltage and current over the predetermined time interval; and means for comparing the measured change in impedance to a preselected threshold, comprising a microprocessor which computes the load impedances from the digital voltage and current values and compares the computed load impedances, wherein said controller takes an action when said comparing means determines that the change in computed load impedance exceeds the threshold.

18. A method for controlling an iontophoretic controller, operatively connected to a patch including at least two electrodes via a respective at least two electrical connectors, the at least two electrodes respectively positioned in an active reservoir and a return reservoir of the patch, said method comprising the steps of:

supplying a current through the patch when the controller is activated;

measuring a change in a voltage across the patch over a predetermined time interval;

measuring a change in current supplied through the patch over the predetermined time interval;

computing a change in load impedance from the measured change in voltage and current over the predetermined time interval; and comparing the measured change in impedance to a threshold, wherein the controller takes an action when the change in computed load impedance exceeds the threshold.

* * * * *

UNITED STATES PATENT AND TRADEMARK OFFICE
CERTIFICATE OF CORRECTION

PATENT NO. : 6,047,208
DATED : April 4, 2000
INVENTOR(S) : Flower

It is certified that error appears in the above-identified patent and that said Letters Patent is hereby corrected as shown below:

Title page,
Item [54], Title, delete "IONTOPHORETIC CONTROLLER" and substitute therefor -- METHOD OF DETECTING EVENTS OR CONDITIONS IN AN IONTOPHORETIC DRUG DELIVERY SYSTEM --

Column 7,
Line 37, delete "Generating" and substitute therefor -- generating --.

Column 8,
Line 12, insert a comma after "to claim 3".
Line 32, after "convert the measured", insert -- voltage --.
Line 46, delete "chance" and substitute therefor -- change --.

Signed and Sealed this

Fourth Day of May, 2004

JON W. DUDAS
*Acting Director of the United States Patent and Trademark Office*